(12) United States Patent
Sato et al.

(10) Patent No.: US 12,237,085 B2
(45) Date of Patent: Feb. 25, 2025

(54) MEDICAL INFORMATION PROCESSING APPARATUS

(71) Applicant: CANON MEDICAL SYSTEMS CORPORATION, Otawara (JP)

(72) Inventors: Kyoko Sato, Nasushiobara (JP); Tatsuo Maeda, Nasushiobara (JP); Yosuke Okubo, Nasushiobara (JP); Daigo Okuhata, Sakura (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 360 days.

(21) Appl. No.: 17/653,025

(22) Filed: Mar. 1, 2022

(65) Prior Publication Data

US 2022/0285031 A1 Sep. 8, 2022

(30) Foreign Application Priority Data

Mar. 2, 2021 (JP) ................................. 2021-032331

(51) Int. Cl.
*G16H 50/30* (2018.01)
*G16H 30/40* (2018.01)
(52) U.S. Cl.
CPC ............. *G16H 50/30* (2018.01); *G16H 30/40* (2018.01)
(58) Field of Classification Search
CPC ...... G16H 50/30; G16H 30/40; G06F 19/324; G06F 19/345; G06F 10/00
See application file for complete search history.

(56) References Cited

U.S. PATENT DOCUMENTS

2017/0154157 A1* 6/2017 Morimoto .............. G16H 50/20
2020/0237452 A1* 7/2020 Wolf ....................... G06F 3/048
2021/0313051 A1* 10/2021 Asselmann ........... G16H 40/67
2022/0359064 A1* 11/2022 Pierson .................. G16H 40/40

FOREIGN PATENT DOCUMENTS

JP WO 2016/006042 A1 1/2016

* cited by examiner

*Primary Examiner* — John J Lee
(74) *Attorney, Agent, or Firm* — Oblon, McClelland, Maier & Neustadt, L.L.P.

(57) ABSTRACT

A medical information processing apparatus comprises processing circuitry. The processing circuitry calculates a functional rate quantitatively indicating a degree as to whether or not a body site related to a symptom of a target patient is properly functioning. The processing circuitry calculates a current state of the target patient as a first state. The processing circuitry estimates, with reference to time-series second medical information having a tendency similar to the first medical information and being related to a similar patient, a likelihood that the state of the target patient may be exacerbated at a future time as a second state, on a basis of a functional rate of the similar patient calculated from a selected part of the second medical information corresponding to time since the similarity to the first medical information was recognized. The processing circuitry causes the first state and the second state to be displayed.

13 Claims, 6 Drawing Sheets

MEDICAL INFORMATION PROCESSING APPARATUS

CROSS-REFERENCE TO RELATED APPLICATIONS

This application is based upon and claims the benefit of priority from Japanese Patent Application No. 2021-032331, filed on Mar. 2, 2021; the entire contents of which are incorporated herein by reference.

FIELD

Embodiments described herein relate generally to a medical information processing apparatus.

BACKGROUND

One of the problems to be solved by the embodiments disclosed in the present specification and drawings is to predict, at an early stage, a likelihood of exacerbation of symptoms of an infectious disease. However, possible problems to be solved by the embodiments disclosed in the present specification and so forth are not limited to the problem presented above. It is also possible to consider any of the problems corresponding to advantageous effects achieved by the configurations described in the embodiments presented below, as other problems to be solved by the embodiments disclosed in the present specification.

DETAILED DESCRIPTION

Exemplary embodiments of a medical information processing apparatus will be explained in detail below, with reference to the accompanying drawings. In the embodiments described below, some of the elements referenced by mutually the same reference characters are assumed to perform mutually the same operations, and duplicate explanations thereof will be omitted as appropriate. Further, the medical information processing apparatus of the present disclosure is not limited to the embodiments described below.

Figure 1:
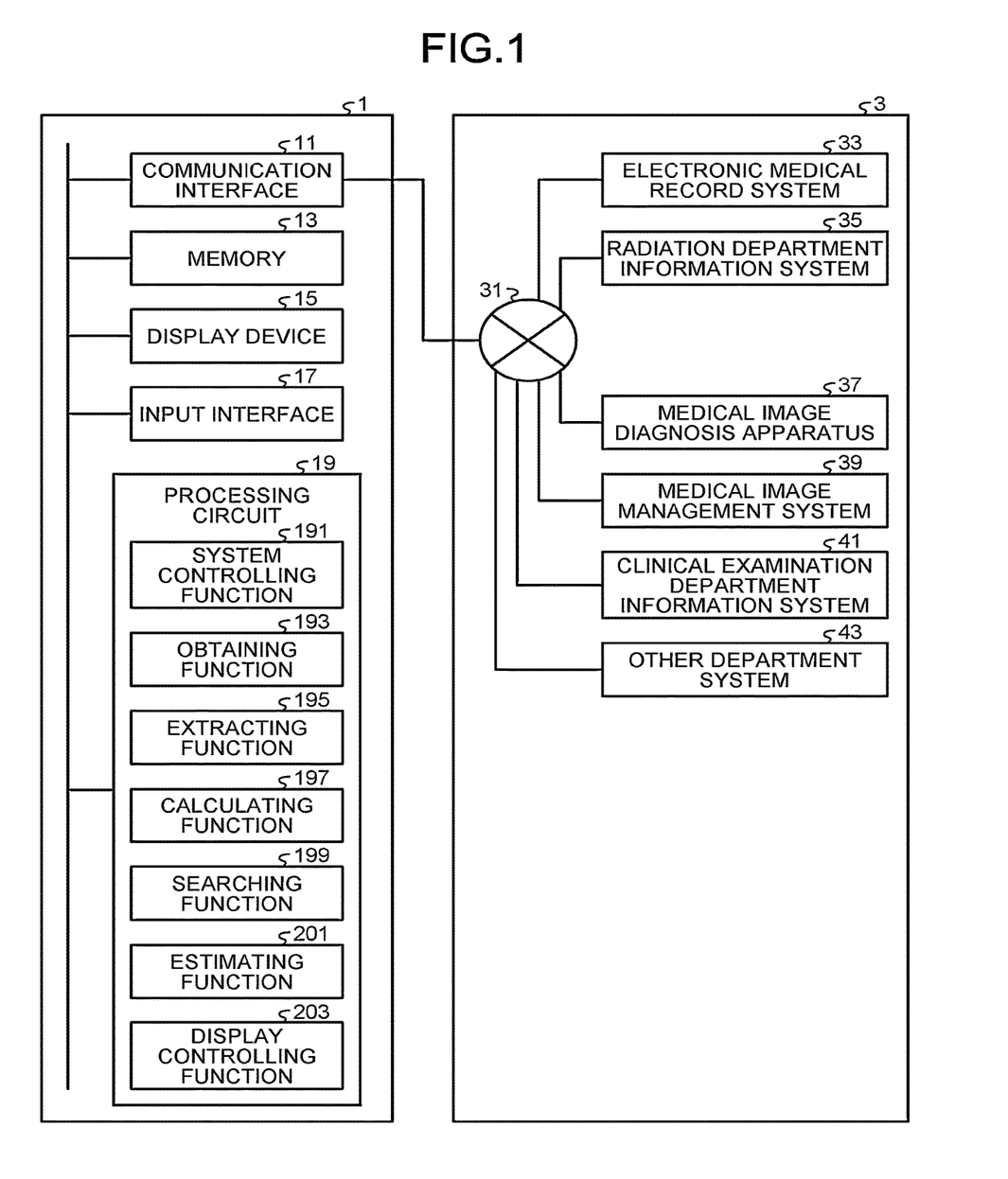
FIG. 1 is a diagram illustrating an exemplary configuration of a medical information processing apparatus according to an embodiment, together with a hospital information system.

An overall configuration of a medical information processing apparatus according to an embodiment will be explained. FIG. 1 is a diagram illustrating an exemplary configuration of a medical information processing apparatus 1 according to the embodiment, together with a Hospital Information System (HIS) 3.

The medical information processing apparatus 1 is connected to the hospital information system 3 via a communication network 31. To begin with, the hospital information system 3 related to the medical information processing apparatus 1 will be explained, before the medical information processing apparatus 1 is explained. The hospital information system 3 includes an electronic medical record system 33, a radiation department information system 35, a medical image diagnosis apparatus 37, a medical image management system 39, a clinical test department information system 41, and an other department system 43.

The electronic medical record system 33, the radiation department information system 35, the medical image diagnosis apparatus 37, the medical image management system 39, and the clinical test department information system 41, and the other department system 43 are connected to one another via a communication network 31 that is either wired or wireless.

The electronic medical record system 33 is an information system configured to manage electronic medical records for recording details of diagnosis/treatment processes. The electronic medical record system 33 includes an electronic medical record server device and an electronic medical record terminal device.

The electronic medical record server device is a computer device configured to perform processes related to managing the electronic medical records. The electronic medical record server device is structured with one or more computer devices, depending on the scale of the system. The electronic medical record terminal device is used by a medical doctor, a nurse, and the like who input and reference the electronic medical records. One or more electronic medical record terminal devices may be provided, depending on the scale of the system. The electronic medical record server device and the electronic medical record terminal device are connected to the communication network 31.

According to an instruction from a user, the electronic medical record terminal device is configured to receive an input of a test order for a patient. When the test order instructs imaging the patient in relation to an image diagnosis process, the test order includes, for example, information related to details of a medical test such as an examined body site (the imaged site), the name of a disease, a purpose of the test, a modality, and/or the like. Further, the test order may include other information such as a patient ID of the patient undergoing the test, the patient's name, a test ID, the date/time of the test, and the like.

In response to the input of the test order, the electronic medical record server device is configured to transmit, to the radiation department information system 35, information related to the test order (hereinafter, "order information"), together with patient information of the patient in the order information and the like. When the test order instructs performing a clinical test on the patient, the electronic medical record server device is configured to transmit the order information to the clinical test department information system 41, in response to the input of the test order.

Test results of all the tests written in the order information will be brought into association with an electronic medical record related to the patient. In this situation, a clinical doctor who made a test request is to provide a diagnosis result on the basis of a test result and to write the diagnosis result into the electronic medical record of the patient. The diagnosis result includes information such as a diagnosis name, a stage, and a seriousness level of the disease. As for the stage and the seriousness level of the disease, a predetermined definition document defines each of different stages and seriousness levels of the disease.

For example, according to an instruction from the clinical doctor, the electronic medical record terminal device is configured to receive an input of the diagnosis result based on various types of tests performed for the patient. The diagnosis result is stored into the electronic medical record server device.

The radiation department information system (a Radiology Information System [RIS]) 35 is an information system configured to manage information in a radiation department in the hospital and includes a radiation department information server device and a radiation department information terminal device. The radiation department information server device is a computer device configured to perform processes related to managing information in the radiation department.

The radiation department information server device is structured with one or more computer devices, depending on the scale of the system. The radiation department information terminal device is used by a laboratory technician or the like in the radiation department. One or more radiation department information terminal devices may be provided, depending on the scale of the system. The radiation department information server device and the radiation department information terminal device are connected to the communication network 31.

In an example of operations, the radiation department information server device is configured to receive the order information from the electronic medical record system 33 and to obtain information about the medical image diagnosis apparatus 37 and the like out of the order information. The radiation department information server device is configured to transmit the order information to the medical image diagnosis apparatus 37 specified in the order information.

In this situation, when transmitting the order information to the medical image diagnosis apparatus 37, the radiation department information server device may add information such as the patient ID and the test date/time to a Digital Imaging and Communications in Medicine (DICOM) tag or the like.

The medical image diagnosis apparatus 37 is an apparatus configured to obtain medical images such as, for example, an X-ray diagnosis apparatus, an X-ray Computed Tomography (CT) apparatus, or a magnetic resonance imaging apparatus. Two or more medical image diagnosis apparatuses 37 may be connected via the communication network 31. On the basis of the test order from the radiation department information system 35, the medical image diagnosis apparatus 37 is configured to perform an imaging process on the patient, in response to an operation performed by a technologist or the like to start the imaging process.

By performing the imaging process, the medical image diagnosis apparatus 37 is configured to acquire data indicating a state of a tissue in the body of the patient. Subsequently, the medical image diagnosis apparatus 37 is configured to generate a medical image on the basis of the data. The medical image diagnosis apparatus 37 is configured to transmit the generated medical image to the medical image management system 39, together with the order information.

The medical image management system (a Picture Archiving and Communication System [PACS]) 39 is an information system configured to manage medical images such as X-ray CT images and MR images. The medical image management system 39 may manage not only post-reconstruction image data, but also pre-reconstruction data (raw data).

The medical image management system 39 includes a medical image management server device. The medical image management server device is a computer device configured to perform processes related to managing the medical images. The medical image management server device is structured with one or more computer devices, depending on the scale of the system. The medical image management server device is connected to the communication network 31.

Upon receipt of the medical image and the order information from the medical image diagnosis apparatus 37, the medical image management server device is configured to store therein the medical image and the order information so as to be kept in association with each other.

The clinical test department information system (a Laboratory Information System [LIS]) 41 is an information system configured to manage information in a clinical test department in the hospital and includes a clinical test department information server device, a clinical test department information terminal device, and a test device.

In the clinical test department information system 41, a specimen test or a biological function test is performed by a clinical laboratory technician, on the basis of the order information transmitted from the electronic medical record system 33. In this situation, the specimen test may be outsourced to an external test institution such as a hygiene inspection laboratory. The clinical test department information server device is a computer device configured to perform processes related to managing information in the clinical test.

The clinical test department information server device is structed with one or more computer devices, depending on the scale of the system. The clinical test department information terminal device is used by a laboratory technician in the clinical test department or the like. One or more clinical test department information terminal devices may be provided, depending on the scale of the system. The clinical test department information server device and the clinical test department information terminal device is connected to the communication network 31.

The test device is a device related to performing the specimen test in which a specimen such as blood or urine collected from the patient is analyzed by the clinical laboratory technician or performing the biological function test in which a brain wave or an electrocardiogram of the patient is taken. In this situation, the specimen test may be, for example, a pathological test, a blood/biochemical test, a general test of urine or stool, an immune serum test, a microorganism test, a test related to blood transfusion or an organ transplant, or the like. The biological function test may be, for example, a brain wave test, a respiratory function test, a cardiac test, a fundoscopy test, or the like.

Two or more test devices may be provided in accordance with the type of the specimen test and the type of the biological function test. At least a part of the specimen test may be performed by an external test institution. In that situation, the clinical test department information server device is configured to receive and store therein an test result related to the specimen test, from the external test institution. Further, the clinical test department information server device is configured to transmit the test result to the electronic medical record system 33.

The other department system 43 may be, for example, a surgery department system, a rehabilitation department system, or a dialysis department system.

In the other department system 43 also, similarly to the radiation department information system 35 and the clinical test department information system 41 described above, a surgery execution report, a rehabilitation execution report, or the like is created in accordance with an order issued by a medical doctor by using the electronic medical record terminal device. The other department system 43 is configured to transmit the surgery execution report or the rehabilitation execution report that was created, to the electronic medical record system 33.

The hospital information system 3 is configured to store therein and manage medical information of patients held in the electronic medical record system 33, the medical image management system 39, the clinical test department information system 41, and the like, so as to be kept in association with patient IDs. More specifically, the hospital information system 3 is configured to store therein and manage, with respect to each of the patient IDs, the medical information related to the patient ID, in the chronological order in which imaging processes and tests were performed. In other words, the medical information of the patients can be referenced in units of points in time or time spans (hereinafter, simply "points in time"). In this situation, the expression "points in time" denotes units of medical consultations such as a medical consultation for the first time, a medical consultation for the second time, and so on.

The medical information processing apparatus 1 is connected to the hospital information system 3 via the communication interface 11 and the communication network 31. Alternatively, the medical information processing apparatus 1 may be incorporated in the hospital information system 3. In an example, the medical information processing apparatus 1 may be used as a report creating device 36.

The medical information processing apparatus 1 illustrated in FIG. 1 includes the communication interface 11, a memory 13, a display 15, the input interface circuit 17, and a processing circuit 19. Data communication among the communication interface 11, the memory 13, the display 15, the input interface circuit 17, and the processing circuit 19 is performed via a bus.

The communication interface 11 is configured to perform data communication with the hospital information system 3. The standard of the communication between the communication interface 11 and the hospital information system 3 may be any standard. It is possible to use, for example, one or both of Health Level 7 (HL7) and DICOM.

The memory 13 is a storage device configured to store therein various types of information, such as a Hard Disk Drive (HDD), a Solid State Drive (SSD), or an integrated circuit storage device. The memory 13 stores therein, for example, data generated as a result of executing an obtaining function 193, an extracting function 195, a calculating function 197, a searching function 199, and an estimating function 201. The generated data and these functions will be explained later.

Further, for example, the memory 13 stores therein a first severity level calculation table used for calculating a first severity level (explained later). Further, the memory 13 stores therein a second severity level calculation table used for calculating a second severity level (explained later).

The memory 13 may be, instead of being an HDD or an SSD, a driving device configured to read and write various types of information from and to a portable storage medium such as a Compact Disc (CD), a Digital Versatile Disc (DVD), or a flash memory, or a semiconductor memory element such as a Random Access Memory (RAM). Further, the memory 13 has stored therein a control program according to the present embodiment.

The display 15 is configured to display various types of information. For example, the display 15 is configured to output a Graphical User Interface (GUI) used for receiving various types of operations from a user. The display 15 is an example of the display apparatus.

For example, as the display 15, it is possible to use, as appropriate, a Liquid Crystal Display (LCD) device, a Cathode Ray Tube (CRT) display device, an Organic Electroluminescence Display (GELD) device, a plasma display device, or any other arbitrary display device, for example.

Further, the display 15 may be of a desktop type or may be configured by using a tablet terminal or the like capable of wirelessly communicating with the main body of the medical information processing apparatus 1.

The input interface circuit 17 is configured to receive various types of input operations from the user, to convert the received input operations into electrical signals, and to output the electrical signals to the processing circuit 19. For example, the input interface circuit 17 is configured to receive, from the user, a selecting instruction or various types of conditions. As the input interface circuit 17, for example, it is possible to use, as appropriate, a mouse, a keyboard, a trackball, a switch, a button, a joystick, a touchpad, a touch panel display device, and/or the like.

In the present embodiment, the input interface circuit 17 does not necessarily have to include physical operation component parts such as a mouse, a keyboard, a trackball, a switch, a button, a joystick, a touchpad, a touch panel display device, and/or the like.

For example, possible examples of the input interface circuit 17 include an electrical signal processing circuit configured to receive an electrical signal corresponding to an input operation from an external input device provided separately from the apparatus and to output the electrical signal to the processing circuit 19. Further, the input interface circuit 17 may be configured by using a tablet terminal or the like capable of wirelessly communicating with the main body of the medical information processing apparatus 1.

In accordance with the electrical signals representing the input operations and being output from the input interface circuit 17, the processing circuit 19 is configured to control operations of the entirety of the medical information processing apparatus 1.

For example, the processing circuit 19 includes, as hardware resources, a processor such as a Central Processing Unit (CPU), a Micro Processing Unit (MPU), and/or a Graphics Processing Unit (GPU), as well as a memory such as a Read-Only Memory (ROM) and/or a RAM.

Further, the processing circuit 19 may be realized by using an Application Specific Integrated Circuit (ASIC), a Field Programmable Gate Array (FPGA), or any of other types of Complex Programmable Logic Devices (CPLDs), a Simple Programmable Logic Device (SPLD), or the like.

The processing circuit 19 includes a system controlling function 191, the obtaining function 193, the extracting function 195, the calculating function 197, the searching function 199, the estimating function 201, and a display controlling function 203.

As for the system controlling function 191, the obtaining function 193, the extracting function 195, the calculating function 197, the searching function 199, the estimating function 201, and the display controlling function 203, the functions are stored in the memory 13 in the form of computer-executable programs.

By employing a processor configured to execute the programs loaded into a memory, the processing circuit 19 is configured to execute the system controlling function 191, the obtaining function 193, the extracting function 195, the calculating function 197, the searching function 199, the estimating function 201, and the display controlling function 203.

That is to say, the processing circuit 19 corresponds to the processor configured to realize the functions corresponding to the programs, by reading and executing the programs from the memory 13. In other words, the processing circuit 19 that has read the programs has the functions corresponding to the read programs.

In this situation, the functions (191, 193, 195, 197, 199, 201, and 203) do not necessarily have to be realized by a single processing circuit. It is also acceptable to structure processing circuitry by combining together a plurality of independent processors, so that the functions (191, 193, 195, 197, 199, 201, and 203) are realized as a result of the processors executing the programs.

The calculating function 197 is an example of the first calculating unit and the second calculating unit. The estimating function 201 is an example of the estimating unit. The display controlling function 203 is an example of the display controlling unit.

The system controlling function 191 is configured to control the functions of the processing circuit 19, on the basis of the input operations received from the user via the input interface circuit 17. More specifically, the system controlling function 191 is configured to read the control program stored in the memory 13, to load the read control program into the memory within the processing circuit 19, and to control functional units of the medical information processing apparatus 1 according to the loaded control program.

The obtaining function 193 is configured to obtain various types of information. For example, the obtaining function 193 is configured to obtain patient information of a patient subject to a diagnosing process (a target patient). The patient information is information such as, for example, a patient ID for identifying each patient, his/her age, gender, height, weight, address, occupation, working form, medical history, current diseases (underlying diseases), current symptoms of the target patient, and/or the like.

More specifically, for example, the obtaining function 193 is configured to obtain the patient information of the patient subject to the diagnosing process, from the electronic medical record system 33 via the communication interface 11. The patient information obtained by the obtaining function 193 is, for example, stored in the memory 13 as first medical information.

Further, for example, the obtaining function 193 is configured to obtain medical image information related to a disease subject to the diagnosing process (e.g., coronavirus disease 2019 [COVID-19]). In the following sections, to explain specific examples, it is assumed that the disease in question (which hereinafter may be referred to as "target disease") is COVID-19. The medical image information is, for example, information including at least one piece of medical image data obtained from a medical image diagnosis apparatus such as an X-ray Computed Tomography (CT) apparatus.

More specifically, for example, the obtaining function 193 is configured to obtain CT image data of a lung region of the target patient taken by an X-ray CT apparatus, from the medical image management system 39 via the communication interface 11. The CT image data obtained by the obtaining function 193 is stored into the memory 13 as first medical information.

Further, for example, the obtaining function 193 is configured to obtain test information related to the target disease. The test information is, for example, information including at least one test result from one or more specimen tests and/or one or more biological function test.

More specifically, for example, the obtaining function 193 is configured to obtain measurement data of the target patient such as a red blood cell count, an HbA1c level, a glycoalbumin level, a Continuous Glucose Monitoring (CGM)/Flash Glucose Monitoring (FGM) value, and/or the like, from the clinical test department information system 41 via the communication interface 11. For example, the measurement data obtained by the obtaining function 193 is stored into the memory 13 as first medical information.

Next, reasons why the red blood cell count, the HbA1c level, the glycoalbumin level, the CGM/FGM value, and/or the like are used as an index of exacerbation of COVID-19 symptoms will be explained. Diabetes is known as one of underlying diseases that can cause exacerbation of COVID-19 symptoms.

Diabetic patients have a possibility of going into an extreme hypoglycemia state by taking medication in a wrong dosage or method, having a meal with inappropriate timing, being in a poor physical condition, or the like. Further, when diabetic patients are in an extreme hypoglycemia state, it is suspected that tissues become anemic and/or less functional due to a decrease in the oxygen transport by red blood cells.

Accordingly, in the present embodiment, the red blood cell count, the HbA1c level, the glycoalbumin level, the CGM/FGM value, and/or the like, which are expected to decrease when the tissues become anemic and/or less functional, are used as an index of exacerbation of COVID-19 symptoms. In other examples, when the target disease is COVID-19, it is also acceptable to use, as an index, a measured value such as an oxygen saturation value or a heartrate, which are each considered to be relevant to exacerbation of COVID-19 symptoms.

Further, it is assumed that it is possible to arbitrarily set the body site or the type of the medical image and the test items of the test information obtained by the obtaining function 193. More specifically, by making it possible to arbitrarily set the medical information obtained by the obtaining function 193 via the input interface circuit 17 or the like, if another disease (e.g., Kawasaki Disease) is newly found to be a cause of exacerbation of COVID-19 symptoms, it is possible to analyze a relationship between the disease and COVID-19 by setting medical information related to the disease as the information to be obtained.

The extracting function 195 is configured to extract a target region of the target disease from each piece of medical image information obtained by the obtaining function 193. For example, the extracting function 195 is configured to extract the target region from CT image data of the target patient.

More specifically, for example, when the target region in the medical image information is the lungs, the extracting function 195 is configured to extract each of the partial regions of the lungs (the right lung upper lobe, the right lung middle lobe, the right lung lower lobe, the left lung upper lobe, and the left lung lower lobe) included in CT image data, by performing a publicly-known segmentation process.

On the basis of the first medical information including the current symptoms of the patient, the calculating function 197 is configured to calculate a functional rate quantitatively indicating a degree as to whether or not a body site related to the current symptoms of the patient is properly functioning. Further, on the basis of the functional rate, the calculating function 197 is configured to calculate the current state of the target patient as a severity level. The severity level is an example of the first state. In this situation, the first medical information includes the medical image information, the test information, and the patient information.

More specifically, for example, with respect to each of the regions extracted by the extracting function 195 such as the right lung upper lobe, the right lung middle lobe, the right lung lower lobe, the left lung upper lobe, and the left lung lower lobe, the calculating function 197 is configured to calculate a first functional rate quantitively indicating a degree as to whether the region is properly functioning, on the basis of the medical image information.

In one example, the first functional rate may be calculated by dividing the difference between the number of pixels in a normal region being a region properly functioning and the number of pixels in an abnormal region being a region in which the function is abnormal, by the number of pixels in the entire region and further multiplying the quotient by 100. In other words, the first functional rate is a value indicating the ratio between the normal region and the abnormal region. For example, when there is no abnormal region in a specific partial region, the calculating function 197 calculates the functional rate of the partial region as 100 percent.

In this situation, the normal region is a region structured with pixels of which the pixel values (brightness values) are equal to or larger than a predetermined threshold value. The abnormal region is a region structured with pixels of which the pixel values are smaller than the threshold value. The threshold value for the pixel values is, for example, an average value or a median value of all the pixels in the region.

As additional information, between the situation where the functional rate of the right lung upper lobe is 50 percent and the situation where the functional rate of the left lung lower lobe is 50 percent, it is considered that there is a difference in how much impact is made on decline in the function of the entire lungs.

Accordingly, with respect to each of the regions of the lungs, the calculating function 197 is configured to determine a correction coefficient (which may be called a "weight") indicating a degree of contribution made to the function of the entire lungs, so as to calculate a corrected first functional rate by multiplying the first functional rate by the correction coefficient.

After that, the calculating function 197 is configured to calculate a first functional rate of the entire lungs on the basis of the corrected first functional rate of each of the regions of the lungs. For example, the calculating function 197 may determine the correction coefficient of each of the regions so that the total is equal to 1, so as to calculate the first functional rate of the entire lungs by adding up the corrected first functional rates of the regions.

In the present embodiment, the calculating function 197 is configured to calculate the first functional rates by dividing the target region into the partial regions; however, possible embodiments are not limited to this example. It is also acceptable to calculate a first functional rate with respect to the entire target region (e.g., the entire lungs), without dividing the target region into sections.

Further, when having calculated the first functional rate of the target region, the calculating function 197 is configured to calculate (specify) a first severity level corresponding to the functional rate of the target region, by referring to a first severity level calculation table in which first functional rates are kept in association with first severity levels based on medical image information. The first severity level calculation table is a table in which the first functional rates are kept in correspondence with the first severity levels, so that the first severity levels increase as the first functional rates decrease, for example.

In the present embodiment, the calculating function 197 is configured to calculate the first severity level by using the first severity level calculation table; however, possible embodiments are not limited to this example. The calculating function 197 may be configured to calculate a first severity level, by using a relational expression defining a relationship between first functional rates and first severity levels. Alternatively, the calculating function 197 may be configured to calculate a first severity level of each of the partial regions, on the basis of the first functional rate of the partial region.

Further, from among the test values of the plurality of test items included in the test information, the calculating function 197 is configured to calculate a second severity level based on the test information, on the basis of one or more of the test values of one or more of the test items related to the disease of the target patient.

More specifically, for example, the calculating function 197 is configured to calculate an observation value from test data and to calculate the second functional rate based on the test information on the basis of the observation value. In this situation, the observation value is a value calculated by subtracting a function limit value from a measured value. Further, the function limit value is a value at which the target region stops functioning when a decrease (or an increase) beyond the value occurs. In this situation, mutually-different function limit values are determined for mutually-different types of tests.

Further, although various types of tests (specimen tests) are performed at medical facilities, there are some test items that have important significance in diagnosing the target disease, and there are other test items that do not need particular attention. Accordingly, the calculating function 197 is configured to determine a correction coefficient indicating a degree of importance for each of the test items and to further calculate a corrected second functional rate by multiplying the second functional rate by the correction coefficient. Because the degrees of importance of the test items vary among mutually-different target diseases, the correction coefficient is determined for each of the target diseases.

The calculating function 197 is configured to calculate a comprehensive second functional rate from the corrected functional rate of each of the tests. More specifically, as the comprehensive second functional rate, the calculating function 197 is configured to calculate an average value of corrected second functional rates of various tests. After that, by referring to a second severity level calculation table in which second functional rates are kept in association with second severity levels, the calculating function 197 is configured to calculate a second severity level corresponding to the calculated second functional rate, as the second severity level.

The second severity level calculation table is a table in which the second functional rates are kept in correspondence with the second severity levels, so that the second severity levels increase as the second functional rates decrease. In the present embodiment, the calculating function 197 is configured to calculate the second severity level by using the second severity level calculation table; however, possible embodiments are not limited to this example. The calculating function 197 may be configured to calculate a second severity level, by using a relational expression defining a relationship between second functional rates and second severity levels. Alternatively, the calculating function 197 may be configured to calculate a second severity level of each of the test items, on the basis of the second functional rate of the test item.

On the basis of the first severity level and the second severity level, the calculating function 197 is configured to calculate a third severity level, which is a comprehensive (final) severity level of the target patient. For example, the calculating function 197 may be configured to calculate the third severity level by calculating an average of the two and rounding up or down to the nearest whole number. In another example, the calculating function 197 may be configured to determine the larger of the first and the second severity levels as the third severity level. In yet another example, the calculating function 197 may be configured to calculate a third severity level after determining a correction coefficient indicating which is considered to be more important between the medical image information and the test information.

The searching function 199 is configured to search for a similar patient whose medical condition is similar to the medical condition of the target patient at the time of a medical consultation. More specifically, the searching function 199 is configured to calculate a level of similarity indicating the degree of similarity between the first medical information of the target patient and the medical information of the patients included in the hospital information system 3 and to search for a patient (hereinafter, "similar patient") having a tendency similar to the first medical information on the basis of the level of similarity.

For example, the searching function 199 conducts a search in (the storage devices of the devices included in) the hospital information system 3 and calculates, for each of the patients, a level of similarity in the medical image information, a level of similarity in the test information, and a level of similarity in the patient information. On the basis of these levels of similarity, the searching function 199 is configured to calculate a comprehensive level of similarity for each of the patients. After that, the searching function 199 is configured to determine at least one patient whose comprehensive level of similarity exceeds a threshold value, as the similar patient. When there is no patient exceeding the threshold value, one of the patients who has the highest level of similarity is determined as the similar patient.

The medical information of the similar patient found in the search conducted by the searching function 199 is stored in the memory 13, for example, as second medical information. The memory 13 is an example of a storage device.

With reference to time-series second medical information of the similar patient, the estimating function 201 is configured to estimate a future state of the target patient as an exacerbation factor, on the basis of a functional rate calculated from a selected part of the second medical information corresponding the time since the similarity to the first medical information was recognized.

The exacerbation factor is an example of the second state. Although the second medical information may or may not include the third severity level, it is assumed in the present embodiment that the second medical information does not include the third severity level.

More specifically, with reference to the time-series second medical information (the medical image information, the test information, and the patient information) of the similar patient stored in the memory 13, the estimating function 201 is configured to estimate a medical condition of the target patient at a future time, by using a selected part of the second medical information corresponding to the time since the similarity to the first medical information was recognized.

Even more specifically, by collaborating with the calculating function 197, the estimating function 201 is configured to calculate, at first, a functional rate at each of different points in time on the basis of the time-series second medical information corresponding to the time since the similarity to the first medical information was recognized. After that, the estimating function 201 is configured to derive a severity level estimated on the basis of the time-series functional rates at the different points in time as the exacerbation factor indicating a likelihood that the state of the target patient may be exacerbated at a future time.

For example, the estimating function 201 may be configured to derive, as the exacerbation factor, a severity level calculated on the basis of a functional rate at the time of the lowest functional rate (at the time of the worst exacerbation) since the similarity to the first medical information was recognized. In other examples, the estimating function 201 may be configured to derive, as the exacerbation factor, an average value of the time-series severity levels at the different points in time or may be configured to derive, as the exacerbation factor, a range from a severity level corresponding to the time of a minimum functional rate to a severity level corresponding to the time of a maximum functional rate.

In this situation, when there are two or more similar patients, the estimating function 201 may derive the exacerbation factor, on the basis of functional rates at different points in time since the similarity to the first medical information was recognized, the functional rates being calculated with respect to each of the similar patients.

In other examples, the estimating function 201 may be configured to derive, as the exacerbation factor, an average of severity levels calculated on the basis of the functional rates at the different points in time calculated with respect to each of the similar patients or may be configured to derive, as the exacerbation factor, the highest severity level among the severity levels calculated on the basis of the functional rates at the different points in time calculated with respect to each of the similar patients.

In yet another example, the estimating function 201 may be configured to derive, as the exacerbation factor, a range from a minimum severity level to a maximum severity level among the severity levels calculated on the basis of the functional rates at the different points in time calculated with respect to each of the similar patients.

Figure 2:
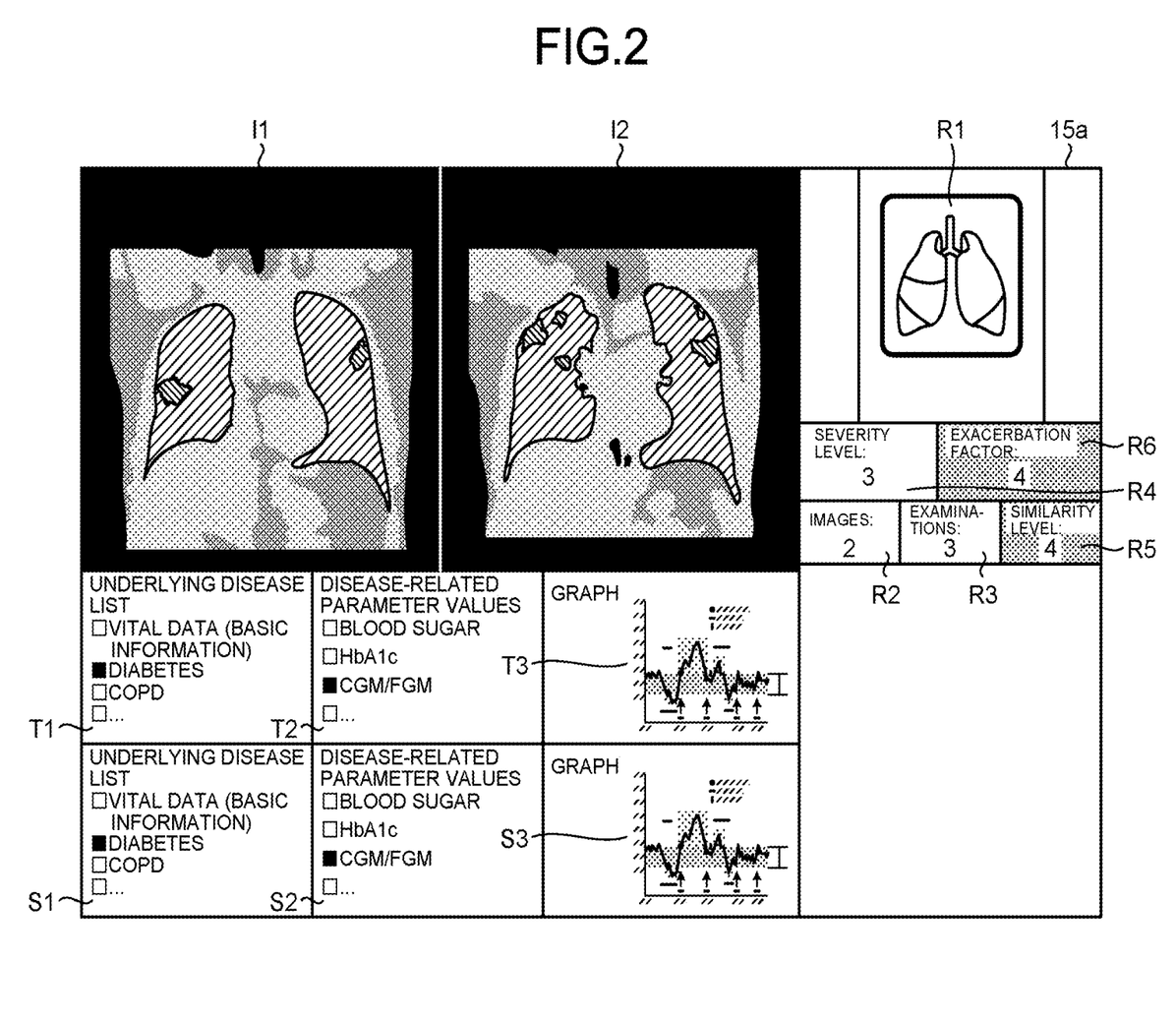
FIG. 2 is a drawing illustrating an example of a display screen indicating a severity level and an exacerbation factor according to the embodiment.
Figure 3:
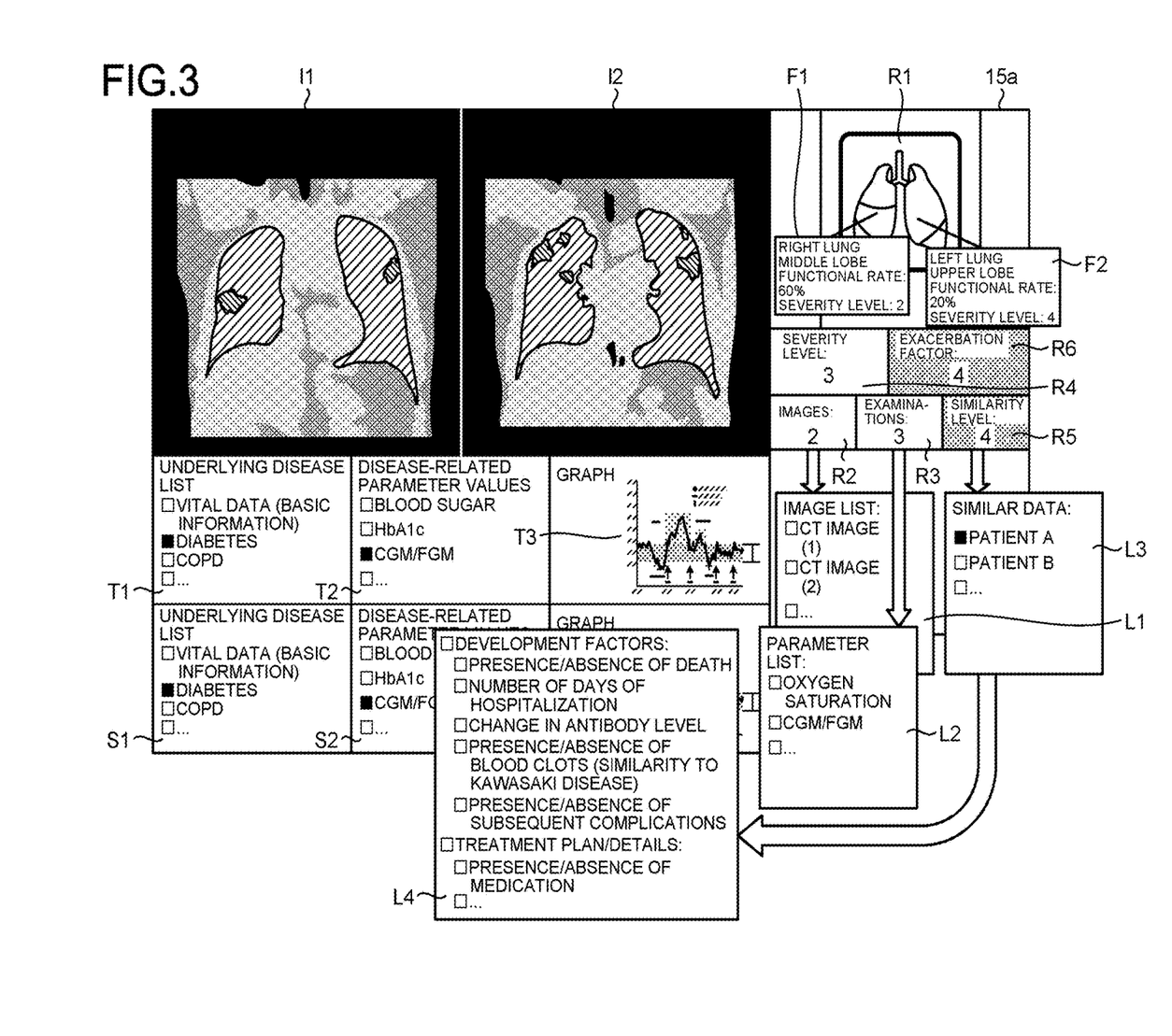
FIG. 3 is a drawing illustrating another example of the display screen indicating the severity level and the exacerbation factor according to the embodiment.

The display controlling function 203 is configured to cause the display 15 to display a screen presenting the severity level and the exacerbation factor related to the target patient. Next, displaying the severity level and the exacerbation factor will be explained, with reference to FIGS. 2 and 3. FIGS. 2 and 3 are drawings illustrating examples of the screen displayed by the display controlling function 203.

As illustrated in FIG. 2, a display screen 15a includes a first medical image display region I1, a second medical image display region I2, a schematic drawing display region R1, a first severity level display region R2, a second severity level display region R3, a third severity level display region R4, a similarity level display region R5, an exacerbation factor display region R6, a first underlying disease list display region T1, a first test item display region T2, a first test result display region T3, a second underlying disease list display region S1, a second test item display region S2, and a second test result display region S3.

The first medical image display region I1 is a region for displaying a medical image (e.g., a CT image of a lung region) of the target patient. In the first medical image display region I1, for example, the most recent medical image or a medical image from which the first severity level was calculated is displayed.

The second medical image display region I2 is a region for displaying a medical image of the similar patient. In the second medical image display region I2, a medical image used for determining the similarity to the target patient or a medical image from which the exacerbation factor was calculated is displayed. When there are two or more similar patients, for example, a medical image of one of the similar patients having the highest similarity level to the target patient may be displayed in the second medical image display region I2. Alternatively, a medical image of one of the similar patients selected from a similar patient list L3 (explained later) may be displayed.

As explained above, the display controlling function 203 is configured to cause the medical image of the target patient and the medical image of the similar patient to be displayed side by side on the display screen 15a. As a result, the user is able to easily compare the medical image of the target patient with the medical image of the similar patient.

Further, the display controlling function 203 is configured to cause the normal region and the abnormal region determined by the calculating function 197 to be displayed in a distinguishable manner, within the displayed medical images of the target patient and the similar patient. For example, the display controlling function 203 may cause the two regions to be displayed in the distinguishable manner, by displaying the normal region and the abnormal region in mutually-different colors. FIG. 2 illustrates an example in which the normal region and the abnormal region are displayed in a distinguishable manner by using mutually-different types of lines in the hatching. As a result, because the normal region and the abnormal region are clearly indicated, the user is able to easily compare the regions (the target regions) each including an abnormal region and the sizes of the normal regions and the abnormal regions, between the target patient and the similar patient.

The schematic drawing display region R1 is a region for displaying a schematic drawing of the target region relevant to the target disease. FIG. 2 illustrates the example where the schematic drawing display region R1 displays the schematic drawing in which the lung region is divided into the partial regions such as the right lung upper lobe, the right lung middle lobe, the right lung lower lobe, the left lung upper lobe, and the left lung lower lobe.

Further, upon receipt of an operation to select one of the partial regions displayed in the schematic drawing display region R1, the display controlling function 203 is configured to cause detailed information to be displayed such as the first functional rate of the target patient calculated with respect to the selected partial region. More specifically, when having received, from the user, an operation to select one from among the right lung upper lobe, the right lung middle lobe, the right lung lower lobe, the left lung upper lobe, and the left lung lower lobe, the display controlling function 203 causes the detailed information of the selected partial region to be displayed.

For example, upon receipt of an input to select the right lung middle lobe from the user, the display controlling function 203 causes detailed information F1 about the right lung middle lobe to be displayed in association with the right lung middle lobe displayed in the schematic drawing display region R1, as illustrated in FIG. 3. For example, the detailed information F1 includes the name of the partial region (RIGHT LUNG MIDDLE LOBE), a first functional rate of the right lung middle lobe calculated by the calculating function 197, and a first severity level calculated from the first functional rate of the right lung middle lobe, or the like.

Further, for example, upon receipt of an input to select the left lung upper lobe from the user, the display controlling function 203 causes detailed information F2 about the left lung upper lobe to be displayed in association with the left lung upper lobe displayed in the schematic drawing display region R1, as illustrated in FIG. 3. Because the content is the same as explained above, explanations thereof will be omitted. Further, although not illustrated in the drawings, the display controlling function 203 performs the same processes as described above upon receipt of an input to select any of the other partial regions from the user. As a result, the user is able to easily check the first functional rate and the first severity level of each of the partial regions, calculated for the target patient.

The method used for selecting each of the partial regions is not particularly limited. For example, the selection may be received through a single click. Alternatively, the selection may be received through an operation of hovering the mouse over the partial region. Further, upon receipt of an input to erase the display of the detailed information from the user (e.g., a single click or an operation to move the mouse away while the detailed information is displayed), the display controlling function 203 is configured to stop displaying the detailed information.

Returning to the description of FIG. 2, the first severity level display region R2 is a region for displaying the first severity level of the target patient calculated on the basis of the medical image information. The display controlling function 203 is configured to cause the first severity level of the target patient calculated by the calculating function 197 from the medical image information to be displayed in the first severity level display region R2.

Further, according to an instruction from the user, the display controlling function 203 is configured to cause a list of the medical images used for calculating the first severity level to be displayed. More specifically, upon receipt of an operation to select the first severity level display region R2 from the user, the display controlling function 203 is configured to cause a medical image list L1 to be displayed in association with the first severity level display region R2, as illustrated in FIG. 3.

As a result, the user is able to easily recognize which medical images were used as a basis for the calculation of the first severity level.

In an example, upon receipt of an input to select one of the medical images in the medical image list L1 from the user, the display controlling function 203 may cause the selected medical image to be displayed in the first medical image display region I1. Further, upon receipt of an input to erase the display of the medical image list L1 from the user (e.g., a single click or an operation to move the mouse away while the medical image list L1 is displayed), the display controlling function 203 is configured to stop displaying the medical image list L1.

Returning to the description of FIG. 2, the second severity level display region R3 is a region for displaying the second severity level of the target patient calculated on the basis of the test information. The display controlling function 203 is configured to cause the second severity level of the target patient calculated by the calculating function 197 to be displayed in the second severity level display region R3.

Further, according to an instruction from the user, the display controlling function 203 is configured to cause a list of the test items used for calculating the second severity level to be displayed. More specifically, upon receipt of an operation to select the second severity level display region R3 from the user, the display controlling function 203 is configured to cause an test item list L2 to be displayed in association with the second severity level display region R3, as illustrated in FIG. 3.

As a result, the user is able to easily check which test items were used as a basis for the calculation of the second severity level.

Further, upon receipt of an input to erase the display of the test item list L2 from the user (e.g., a single click or an operation to move the mouse away while the test item list L2 is displayed), the display controlling function 203 is configured to stop displaying the test item list L2.

Returning to the description of FIG. 2, the third severity level display region R4 is a region for displaying the final severity level of the target patient. The display controlling function 203 is configured to cause the final severity level calculated by the calculating function 197 to be displayed in the third severity level display region R4.

The similarity level display region R5 is a region for displaying a similarity level between the target patient and the similar patient. The display controlling function 203 is configured to cause the comprehensive similarity level calculated by the estimating function 201 to be displayed in the similarity level display region R5.

Further, according to an instruction from the user, the display controlling function 203 is configured to cause a list of the similar patients found in the search conducted by the searching function 199 to be displayed. More specifically, upon receipt of an input to select the similarity level display region R5 from the user, the display controlling function 203 is configured to cause the similar patient list L3 to be displayed while being superimposed on the display screen 15*a* indicating the severity level and the exacerbation factor, as illustrated in FIG. 3.

In the similar patient list L3, the display controlling function 203 is configured to cause the list of the similar patients found in the search conducted by the searching function 199 to be displayed. Further, when the similar patient list L3 displays two or more similar patients, the display controlling function 203 is configured to receive, from the user, an input to select one of the similar patients. Processes to be performed after one of the similar patients is selected will be explained later.

In this situation, upon receipt of an input to erase the display of the similar patient list L3 from the user (e.g., a single click or an operation to move the mouse away while the similar patient list L3 is displayed), the display controlling function 203 is configured to stop displaying the similar patient list L3.

Further, according to an instruction from the user, the display controlling function 203 is configured to cause development factors to be displayed regarding symptoms related to the target disease of the similar patient. More specifically, when being instructed to display the development factors of one of the similar patients on the basis of the similar patient list L3, the display controlling function 203 is configured to display a development factor display element L4 of the selected similar patient, as illustrated in FIG. 3.

The development factors are information including, for example, whether or not the similar patient died, how many days of hospitalization, a transition of measurement results from quantitative antibody tests, whether blood clots were observed (whether symptoms similar to those of Kawasaki Disease were observed), whether subsequent complications were present/absent, and/or the like. Further, in addition to the development factors, the display controlling function 203 may cause the development factor display element L4 to display information about treatment such as whether or not a medication was administered (and, if yes, the type of the drug, the administered amount, and the frequency of the administration).

As a result, the user is able to easily learn the progress of the target disease of the similar patient. It is therefore possible to use the obtained information for treatment of the target patient.

Further, as for an instruction to have the development factors displayed, for example, a development factor display button or the like may be displayed on the display screen 15*a*, so that the display is realized in accordance with an operation performed on the development factor display button. Further, upon receipt of an input to erase the display of the development factor display element L4 (e.g., a single click or an operation to move the mouse away while the development factor display element L4 is displayed), the display controlling function 203 is configured to stop displaying the development factor display element L4.

Returning to the description of FIG. 2, the exacerbation factor display region R6 is a region for displaying the exacerbation factor of the target patient. The display controlling function 203 is configured to cause the exacerbation factor calculated by the estimating function 201 to be displayed in the exacerbation factor display region R6.

The first underlying disease list display region T1 is a region for displaying information related to underlying diseases of the target patient. More specifically, the display controlling function 203 is configured to cause a list of underlying diseases that are included in the patient information and are relevant to the target disease to be displayed in the first underlying disease list display region T1.

In FIG. 2 (FIG. 3), an example is illustrated in which the target patient is suffering from diabetes as the underlying disease. In this situation, because the patient information of the target patient includes information indicating that he/she is suffering from diabetes, the display controlling function 203 displays information with a check mark next to "diabetes" in the underlying disease list, on the basis of the underlying disease in the patient information. As a result, it is understood that the target patient is suffering from diabetes. Further, the display controlling function 203 displays the other underlying diseases such as Chronic Obstructive Pulmonary Disease (COPD) without check marks, because the target patient is not suffering from those diseases. Accordingly, it is understood that the target patient is not suffering from COPD.

Further, the first test item display region T2 is a region for displaying an test item related to the calculation of the second severity level of the target patient. For example, the display controlling function 203 is configured to cause one of the test items selected by the user to be displayed in the first test item display region T2.

More specifically, the display controlling function 203 is configured to cause all the test items relevant to the target disease to be displayed in the first test item display region T2. When the user inputs a selection from among the test items, the display controlling function 203 displays a check mark with the selected test item. In the examples in FIGS. 2 and 3, the display controlling function 203 has a check mark displayed with the "CGM/FGM" displayed in the first test item display region T2.

The first test result display region T3 is a region for displaying an test result of the test item displayed in the first test item display region T2. More specifically, when a check mark is displayed with the "CGM/FGM" displayed in the first test item display region T2, the display controlling function 203 is configured to cause a graph indicating time-series changes in measurement results of CGM/FGM to be displayed in the first test result display region T3.

The second underlying disease list display region S1 is a region for displaying information related to underlying diseases of the similar patient. The second test item display region S2 is a region for displaying one of the test items focused on by the user, from among the test items used for calculating the exacerbation factor of the similar patient. The second test result display region S3 is a region for displaying an test result of the test item displayed in the second test item display region S2.

Because what is displayed in the second underlying disease list display region S1, the second test item display region S2, and the second test result display region S3 is similar to what is displayed in the first underlying disease list display region T1, the first test item display region T2, and the first test result display region T3, respectively, the explanations thereof will be omitted. In this situation, it is possible to select, via the similar patient list L3 for example, the similar patient whose information is displayed in the second underlying disease list display region S1, the second test item display region S2, and the second test result display region S3.

As explained above, the display controlling function 203 is configured to cause the underlying diseases, the measurement data of the test items, and the like to be displayed side by side, with respect to the target patient and the similar patient. With this arrangement, the user is able to easily compare the underlying diseases and the measurement data between the target patient and the similar patient.

Figure 4:
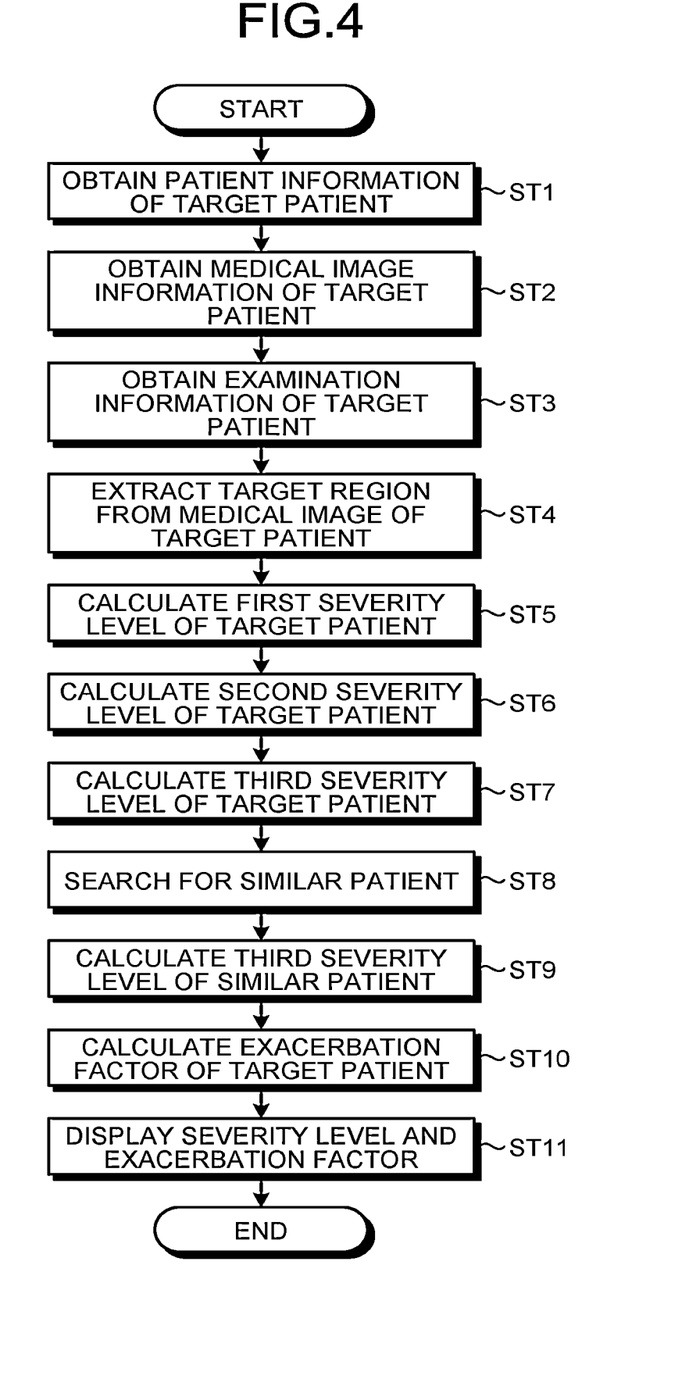
FIG. 4 is a flowchart illustrating an example of processes performed by the medical information processing apparatus according to the embodiment.

Next, processes performed by the medical information processing apparatus 1 described above will be explained. FIG. 4 is a flowchart illustrating an example of the processes performed by the medical information processing apparatus 1.

To begin with, from the hospital information system 3, the obtaining function 193 obtains information about the target patient such as his/her patient ID, age, gender, height, weight, address, occupation, working form, medical history, names of underlying diseases, symptoms, and the like, as patient information (step ST1). The patient information obtained by the obtaining function 193 is stored into the memory 13 as first medical information.

From the electronic medical record system 33, the obtaining function 193 obtains CT image data of the lung region of the target patient, as medical image information (step ST2). The medical image information obtained by the obtaining function 193 is stored into the memory 13 as first medical information.

From the electronic medical record system 33, the obtaining function 193 obtains measurement data of the target patient such as a red blood cell count, a HbA1c level, a glycoalbumin level, a CGM/FGM value, an oxygen saturation value, a heartrate, and/or the like, as test information (step ST3). The test information obtained by the obtaining function 193 is stored into the memory 13, as first medical information.

By performing a segmentation process, the extracting function 195 extracts each of the partial regions (the right lung upper lobe, the right lung middle lobe, the right lung lower lobe, the left lung upper lobe, and the left lung lower lobe) of the lungs included in the CT image data of the lung region of the target patient obtained by the obtaining function 193 (step ST4).

With respect to each of the partial regions extracted by the extracting function 195, the calculating function 197 calculates a first functional rate. The calculating function 197 calculates the first severity level of the entire lung region by integrating together the first functional rates of the partial regions (step ST5).

On the basis of the test information obtained by the obtaining function 193, the calculating function 197 calculates a second functional rate with respect to each of the test items. The calculating function 197 calculates a second severity level of the entire test information by integrating together the second functional rates of the test items (step ST6).

On the basis of the first severity level calculated at step ST5 and the second severity level calculated at step ST6, the calculating function 197 calculates a third severity level (step ST7).

By using the medical image and the measurement result of the test item included in the first medical information as a search key, the searching function 199 searches in the hospital information system 3 for a similar patient having data that is the same as or similar to the search key (step ST8). The medical information of the similar patient found in the search conducted by the searching function 199 is stored into the memory 13 as second medical information.

With reference to the second medical information of the similar patient found in the search conducted by the searching function 199, the estimating function 201 causes the calculating function 197 to calculate a third severity level of the similar patient, on the basis of a selected part of the second medical information obtained since the similarity to the target patient was recognized (step ST9).

The estimating function 201 calculates an exacerbation factor on the basis of the third severity level of the similar patient calculated by the calculating function 197 (step ST10).

On the basis of the third severity level calculated by the calculating function 197 and the exacerbation factor calculated by the estimating function 201, the display controlling function 203 causes the display 15 to display the display screen 15a explained above and thus ends the present processes (step ST11).

In the medical information processing apparatus 1 according to the embodiment described above, the calculating function 197 is configured to calculate the state of the disease from which the target patient is suffering as the severity level, on the basis of the first medical information obtained from the target patient. The estimating function 201 is configured to estimate the state of the target patient at a future time as the exacerbation factor, on the basis of the second medical information of the similar patient having the elements similar to those in the first medical information, from the storage device storing therein the second medical information of the patient who is undergoing a diagnosis/treatment process or has finished a diagnosis/treatment process. The display controlling function 203 is configured to cause the display 15 to display the severity level and the exacerbation factor.

As a result, because the calculating function 197 is configured to calculate the severity level of the target patient, the user such as a medical doctor is able to learn the current medical condition of the target patient in the form of the objective numerical values. Further, when the severity level of the target patient calculated by the calculating function 197 is available, the estimating function 201 is able to calculate the exacerbation factor of the target patient. Accordingly, even when the target patient is having a medical consultation for the first time, for example, it is possible to estimate, to a certain extent, the medical condition of the target patient at a future time.

In other words, the medical information processing apparatus 1 according to the present embodiment is capable of predicting, at an early state, the likelihood of exacerbation of symptoms of the infectious disease.

Further, it is also possible to carry out the embodiments described above with modifications, as appropriate, by changing a part of the configurations and/or the functions of the apparatuses and the devices. Thus, in the following sections, a number of modification examples of the above embodiments will be explained as other embodiments. In the following sections, differences from the above embodiments will primarily be explained. Detailed explanations of some of the features that are the same as those already explained will be omitted. Further, the modification examples described below may individually be carried out or may be carried out in combination, as appropriate.

First Modification Example

In the above embodiments, the example was explained in which the calculating function 197 is configured to calculate the first functional rate, by using the average value or the median value of the pixel values of all the pixels in the region as the threshold value for the pixel values; however, it is also acceptable to allow the user to set a threshold value for the pixel values.

Figure 5:
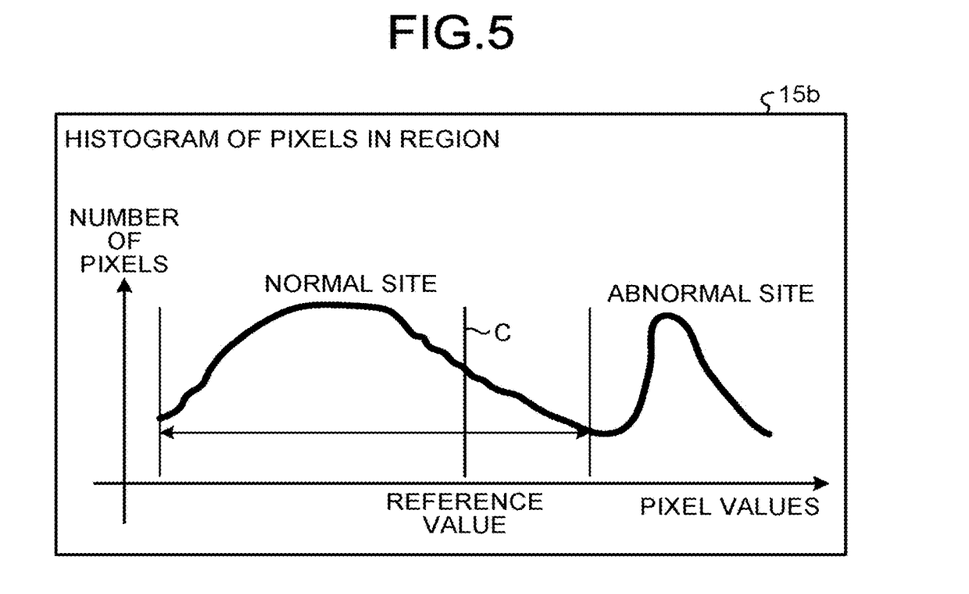
FIG. 5 is a drawing illustrating an example of a screen for setting a threshold value for pixel values according to a first modification example.

In that situation, the calculating function 197 is configured to display a histogram of the pixels in a partial region, for example, so as to prompt the user to designate a threshold value (a reference value) for the normal region. FIG. 5 is a drawing illustrating an example of a screen for setting the threshold value for the pixel values. On a threshold value setting screen 15b, the display controlling function 203 is configured to display the histogram of the pixels in the partial region.

Further, on the threshold value setting screen 15b, the display controlling function 203 is configured to display a selecting cursor C. The user can input a confirmation of the threshold value (the reference value) by moving the selecting cursor C to an arbitrary position. The calculating function 197 is configured to calculate a first functional rate by using the threshold value (the reference value) determined by the user.

According to the present modification example, the user is able to check the distribution of the pixel values in the region. Accordingly, for example, even in the situations where it would be inappropriate to use the average value or the median value as the threshold value (e.g., the distribution of the pixel values is so biased that an extremely large number of abnormal regions would be found if the average value or the median value were used as the threshold value), it is possible to set an appropriate value as the threshold value on the basis of the distribution of the pixel values.

Second Modification Example

In the above embodiments, the example was explained in which, by using the CT image data, the extracting function 195 is configured to divide and extract, from the lung region, the partial regions (the right lung upper lobe, the right lung middle lobe, the right lung lower lobe, the left lung upper lobe, and the left lung lower lobe). However, the extracting function 195 may be configured to extract a part related to an underlying disease such as COPD or a part involving a characteristic observation, as an abnormal region.

Figure 6:
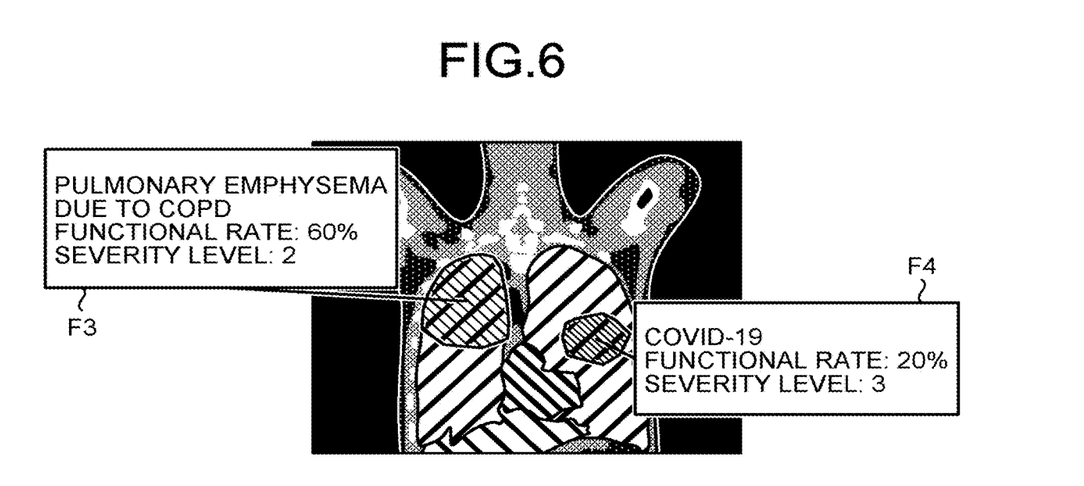
FIG. 6 is a drawing illustrating an example of medical image information according to a second modification example.

The present modification example will be explained by using a target patient whose CT image data exhibits pulmonary emphysema due to COPD in the right lung upper lobe and involves a characteristic observation of COVID-19 in the left lung upper lobe. FIG. 6 is a drawing illustrating an example of the medical image information according to a second modification example.

From the CT image data, the extracting function 195 is configured to extract the region in which the pulmonary emphysema due to COPD is observed as an abnormal region. Further, from the CT image data, the extracting function 195 is configured to extract the region involving the characteristic observation of COVID-19, as another abnormal region.

The calculating function 197 is configured to calculate first functional rates with respect to the region exhibiting the pulmonary emphysema due to COPD and to the region involving the characteristic observation of COVID-19. Further, the calculating function 197 is configured to individually calculate a first severity level with respect to each of the abnormal regions.

In the CT image data, the display controlling function 203 is configured to display the region exhibiting the pulmonary emphysema due to COPD and the region involving the characteristic observation of COVID-19 in a distinguishable manner (e.g., by displaying the regions in mutually-different colors).

Further, the display controlling function 203 is configured to display detail display regions F3 and F4. In the detail display regions F3 and F4, the display controlling function 203 is configured to display the names of the diseases (the names of the observed characteristics), the (first) functional rates, and the (first) severity levels.

In the present example, in the detail display region F3, the display controlling function 203 displays "PULMONARY EMPHYSEMA DUE TO COPD; FUNCTIONAL RATE: 60%; SEVERITY LEVEL: 2". In the detail display region F4, the display controlling function 203 displays, "COVID-19, FUNCTIONAL RATE 20%; SEVERITY LEVEL: 3".

According to the present modification example, it is possible to understand the state of the diseased sites, which is difficult to understand from the first functional rates and the first severity levels of the partial regions extracted while paying attention to the forms. For example, when the diseased sites extend over a plurality of partial regions, impacts of the disease are difficult to be visualized, because the impacts of the disease are distributed among the partial regions. In contrast, in the present modification example, because the calculating function 197 is configured to calculate the first functional rates and the first severity levels while paying attention to the diseased parts, the user is able to accurately understand how much the functions of the diseased parts have declined.

Third Modification Example

In the above embodiments, the example was explained in which the estimating function 201 is configured to estimate the medical condition of the target patient at a future time, on the basis of the second medical information. However, the estimating function 201 may be configured to estimate a medical condition of the target patient at a future time, on the basis of chronological changes in the target disease exhibited in the first medical information.

Figure 7:
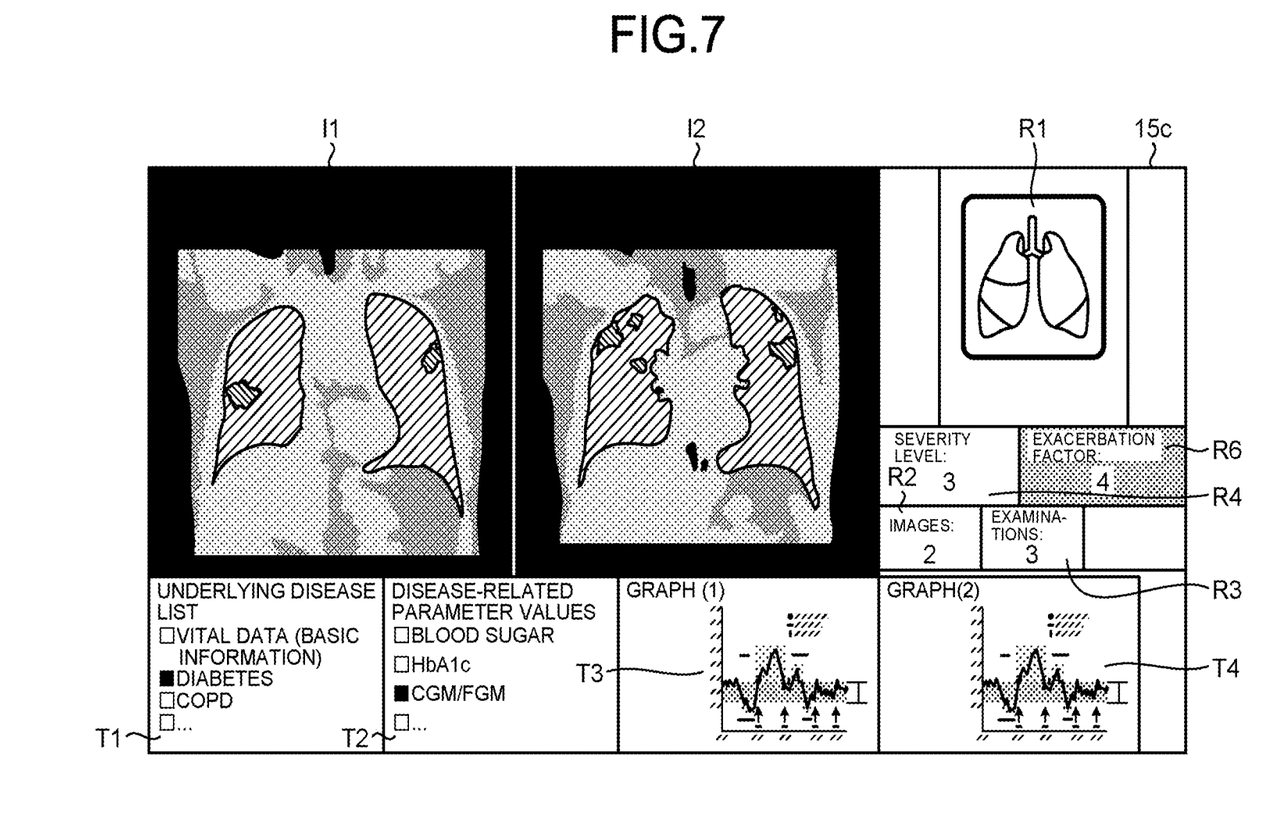
FIG. 7 is a drawing illustrating an example of a display screen indicating a severity level and an exacerbation factor according to a third modification example.

FIG. 7 is a drawing illustrating an example of a display screen according to a third modification example. On a display screen 15c according to the third modification example, the display controlling function 203 is configured to display a past test result display region T4, in place of the second underlying disease list display region S1, the second test item display region S2, and the second test result display region S3. Further, in the second medical image display region I2, a medical image of the target patient taken in the past is displayed.

In the past test result display region T4, the display controlling function 203 is configured to display measurement data of the target patient from the past, with respect to the test item displayed in the first test item display region T2. Because the most recent data and the past data of the target patient are displayed side by side, the user is able to more easily understand chronological changes in the target disease of the target patient.

In an example, the display controlling function 203 may be configured to have two or more pieces of measurement data from the past to be displayed side by side with the most recent data.

According to the present modification example, the estimating function 201 is configured to estimate a medical condition of the target patient at a future time, on the basis of the progress of the disease of the target patient himself/herself, it is expected to be possible to estimate the medical condition of the target patient at the future time with a higher level of precision.

Fourth Modification Example

In the above embodiments, the example was explained in which the calculating function 197 is configured to calculate the first functional rate, on the basis of the ratio between the normal region being the region functioning properly and the abnormal region being the region in which the function is abnormal that were extracted from the target region related to the disease of the target patient. However, the calculating function 197 may be configured to calculate a first functional rate, by using a trained model generated through a method implementing deep learning or another type of machine learning.

In this situation, it is assumed that the trained model is a model that has learned medical image information in correspondence with first functional rates. The calculating function 197 is configured to input the medical image information (e.g., one or more pieces of CT image data) to the trained model and to calculate a first functional rate output by the trained model as the first functional rate.

Fifth Modification Example

In the above embodiments, the example was explained in which the calculating function 197 is configured to calculate the second functional rate on the basis of the test value and the coefficient determined in advance with respect to each of the test items. However, the calculating function 197 may be configured to calculate a second functional rate by using a trained model generated through a method implementing deep learning or another type of machine learning.

In this situation, it is assumed that the trained model is a model that has learned test information (one or more pieces of measurement data) in correspondence with second functional rates. The calculating function 197 is configured to input the test information (e.g., one or more pieces of measurement data) to the trained model and to calculate a second functional rate output by the trained model as the second functional rate.

Sixth Modification Example

In the above embodiments, the example was explained in which the calculating function 197 is configured to calculate the first severity level on the basis of the first functional rate, to calculate the second severity level on the basis of the second functional rate, and to calculate the third severity level on the basis of the first severity level and the second severity level. However, the calculating function 197 may be configured to calculate a third severity level, by using a trained model generated through a method implementing deep learning or another type of machine learning.

In this situation, it is assumed that the trained model is a model that has learned medical image information, test information, and third severity levels in correspondence with one another. The calculating function 197 is configured to input the medical image information (e.g., one or more pieces of CT image data) and the test information (e.g., one or more pieces of measurement data) to the trained model and to calculate a third severity level output by the trained model as the third severity level.

Alternatively, the calculating function 197 may be configured to calculate a first severity level by inputting the medical image information to a trained model that has learned medical image information in correspondence with first severity levels, to further calculate a second severity level by inputting the test information to a trained model that has learned test information in correspondence with second severity levels, so as to further calculate a third severity level on the basis of the first severity level and the second severity level.

According to at least one aspect of the embodiments described above, it is possible to predict, at an early stage, the likelihood of exacerbation of the symptoms of the infectious disease.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus, comprising:

processing circuitry configured to:
calculate, based on first medical information including a current symptom of a target patient, a functional rate quantitively indicating a degree as to whether or not a body site related to the current symptom is properly functioning;

calculate, based on the functional rate of the target patient, a current state of the target patient as a first state;

estimate, with reference to time-series second medical information having a tendency similar to the first medical information and being related to a similar patient, a likelihood that the current state of the target patient may be exacerbated at a future time [as] to a second state, based a functional rate of the similar patient calculated from a selected part of the second medical information corresponding to a time since the similarity to the first medical information was recognized; and cause the first state and the second state to be displayed.

2. The medical information processing apparatus according to claim 1, wherein from a target region related to a disease of the target patient within a region of the target patient rendered in medical image information that is obtained by imaging the target patient and included in the first medical information, the processing circuitry is further configured to extract a normal region being a region properly functioning and an abnormal region being a region in which the function is abnormal, and the processing circuitry is further configured to calculate the functional rate based a ratio between the extracted normal region and the extracted abnormal region.

3. The medical information processing apparatus according to claim 2, wherein the processing circuitry is further configured to:

divide the target region into a plurality of partial regions, calculate the ratio between the normal region and the abnormal region with respect to each of the partial regions, and calculate the functional rate based the ratio calculated with respect to each of the partial regions.

4. The medical information processing apparatus according to claim 3, wherein the processing circuitry is further configured to:

calculate the ratio between the normal region and the abnormal region with respect to each of the partial regions, calculate the functional rate based on the ratio calculated with respect to each of the partial regions, and calculate the first state based on the calculated functional rate and a coefficient determined in advance with respect to each of the partial regions.

5. The medical information processing apparatus according to claim 3, wherein the processing circuitry is further configured to cause a display to display an image indicating each of the partial regions, and the processing circuitry is further configured to cause a ratio between the normal region and the abnormal region calculated with respect to each of the partial regions to be displayed in association with a corresponding one of the partial regions.

6. The medical information processing apparatus according to claim 2, wherein the processing circuitry is further configured to cause a display to display, in a comparable manner, the medical image information of the target patient and medical image information of the similar patient.

7. The medical information processing apparatus according to claim 2, wherein the processing circuitry is further configured to cause a display to display the medical image information of the target patient and further cause the normal region and the abnormal region to be displayed in a distinguishable manner while being superimposed on the medical image information.

8. The medical information processing apparatus according to claim 1, wherein, from among test values of a plurality of examination items that are obtained by examining the target patient and included in the first medical information, the processing circuitry is further configured to calculate the functional rate based on one or more of the test values of one or more of the test items related to the disease of the target patient.

9. The medical information processing apparatus according to claim 8, wherein when there are two or more test items related to the disease of the target patient, the processing circuitry is further configured to calculate the functional rate based on the test values of the test items related to the disease of the target patient, and the processing circuitry is further configured to calculate the first state based on the calculated functional rate and a coefficient determined in advance with respect to each of the test items.

10. The medical information processing apparatus according to claim 8, wherein the processing circuitry is further configured to cause a display to display, in a comparable manner, test information of the target patient and test information of the similar patient.

11. The medical information processing apparatus according to claim 1, wherein, when time-series second medical information of the target patient is present, the processing circuitry is further configured to estimate the second state based on a chronological change in a disease of the target patient exhibited in the time-series second medical information.

12. The medical information processing apparatus according to claim 11, wherein the processing circuitry is further configured to cause a display to display the chronological change in the disease of the target patient.

13. The medical information processing apparatus according to claim 1, wherein the first medical information includes at least one of medical image information or test information, the medical image information indicating the current symptom of the target patient and obtained by imaging the target patient, the test information obtained by examining the target patient, and the processing circuitry is further configured to calculate, based on the first medical information, a functional rate quantitatively indicating a degree as to whether or not a body site of the target patient related to the symptom indicated by the first medical information is properly functioning.

* * * * *